United States Patent [19]
Harrison

[11] Patent Number: 5,546,961
[45] Date of Patent: Aug. 20, 1996

[54] STERILITY MAINTENANCE COVER AND INSTRUMENT SUPPORT

[76] Inventor: Samuel W. Harrison, 4003 Scenic Dr., Shreveport, La. 71119

[21] Appl. No.: 540,470

[22] Filed: Oct. 10, 1995

[51] Int. Cl.$^6$ .............................. A61B 19/00; A61F 11/00
[52] U.S. Cl. ............................................ 128/849; 128/857
[58] Field of Search ................................. 128/857, 849, 128/845, 846, 858, 852, 856, 205.56; 5/507.1; 248/174; D15/126

[56] References Cited

U.S. PATENT DOCUMENTS

| | | | |
|---|---|---|---|
| 3,557,791 | 1/1971 | Duffy | 128/845 |
| 3,889,670 | 6/1975 | Loveland | 128/204 |
| 4,003,378 | 1/1977 | Ackering | 128/204 |
| 4,018,217 | 4/1977 | Evans | 128/1 R |
| 4,275,719 | 6/1981 | Mayer | 128/132 |
| 4,936,318 | 6/1990 | Schoolman | 128/847 |
| 5,005,590 | 4/1991 | Eldridge | 128/849 |
| 5,195,538 | 3/1993 | Eldridge | 128/849 |
| 5,316,541 | 5/1994 | Fischer | 128/849 |
| 5,322,072 | 6/1994 | Harrison | 128/849 |
| 5,360,018 | 11/1994 | Chen | 128/849 |
| 5,396,904 | 3/1995 | Hartigan | 128/849 |

OTHER PUBLICATIONS

Interiors Magazine, p. 52 Dec., 1973 issue.

Primary Examiner—Michael A. Brown
Attorney, Agent, or Firm—John M. Harrison

[57] ABSTRACT

A device for maintaining the sterility of a patient and supporting medical instruments during both invasive and non-invasive procedures, which device includes a generally L-shaped member having a base panel for fitting beneath a patient and a supporting surface such as an operating table, an upward-standing side or end panel extending from the base panel and provided with an open window for accessing the patient and a horizontally-oriented instrument platform extending from the end panel parallel to the base panel above the patient's head, neck and shoulders, for receiving and deploying a drape and/or instruments during surgery. Gussets may extend from each edge of the base panel along the end panel to the instrument platform to strengthen the instrument platform. The device facilitates draping of the patient's head and upper body to insure a sterile operating field which is maintained throughout the procedure and the instrument platform facilitates deployment of surgical and other instruments in an efficient manner. In a preferred embodiment, the instrument panel, end panel and base panel are constructed of a single piece of transparent, radiolucent material such as ABS plastic.

20 Claims, 1 Drawing Sheet

STERILITY MAINTENANCE COVER AND INSTRUMENT SUPPORT

BACKGROUND OF THE INVENTION

1. Field of the Invention

During invasive surgical procedures such as pacemaker implants and similar procedures, it is imperative that the patient's head be draped in a sterile manner to insure that a sterile field is maintained throughout the operation. Various methods have been employed to achieve this result, including various types of draping techniques, supports and other devices. The sterility maintenance cover and instrument support of this invention is designed not only for optimum effectiveness in achieving sterility during certain types of operating procedures, but also to support surgical and other instruments in an efficient manner, in emergency room, intensive care, operating room, home health care and examination room applications. The apparatus includes a generally L-shaped, transparent support having a base panel for fitting under the head, neck and shoulders of a patient positioned on an examination or operating table, an upward-standing end panel extending from the base panel and having an open window for accessing the patient from the end or side of the table and an instrument panel or platform projecting horizontally from the end panel, substantially parallel to the base panel over the patient's head and neck. Gussets may extend from the base panel along the end panel to support the instrument panel. The instrument platform is designed to support one or more drapes and/or to receive and retain or deploy various instruments used in the designated examination, I.V. or surgical procedure and may be fitted with an upward-standing, peripheral lip to maintain the instruments in position on the instrument platform. The sterility maintenance cover and instrument support is preferably constructed of a radiolucent plastic material such as ABS plastic, polycarbonate or other such plastic material, with the base panel, end panel and instrument platform most preferably shaped from a single sheet of transparent plastic material.

2. Description of the Prior Art

Various devices are known in the art for enclosing or partially enclosing patients for various purposes. For example, a non-invasive hyperbaric ventilator is detailed in U.S. Pat. No. 3,889,670 dated Jun. 17, 1975, to Steven R. Loveland, et al for alleviating bronchopulmonary disorders in patients. The device includes a plexiglass chamber, into which the patient's head is inserted. A collar assembly around the patient's neck seals the chamber and an adjustable pressure gauge for regulating gas delivery pressures to the chamber and an expiratory resistance valve cooperate to provide intermittent pressurization and depressurization of the ventilator. The chamber is provided with multiple studs and ports to accommodate attachment of various accessory devices. U.S. Pat. No. 4,003,378, dated Jan. 18, 1977, to Donald E. Pickering, details a Transport and Life-Support System for Infants. The system includes a semi-rigid tray having a detachable bumper and a rigid transparent life support hood releasably attached to the tray and provided with ports for the introduction of air and oxygen into the hood and for the attachment of a pressure regulating device thereto. The hood is adapted to receive the head and chest of the infant and is adhesively sealed to the chest with a reinforced plastic material. U.S. Pat. No. 4,275,719, dated Jun. 30, 1981, to Nathan Mayer, details an "Apparatus and Method for Providing An Aseptic Surgical Environment". A patient is first wrapped with a plastic film sheet which is adhesively sealed to the patient's body remote from an operating area on the body and is also sealed against an incision site on the body at the operating area. A sterilized atmosphere is provided beneath the film sheet for contacting the patient's skin. Another sterilized atmosphere is provided within a region substantially adjacent to the body, including the incision site, thereby enabling a surgeon to cut through the film sheet and into the patient's body with minimal risk of infection. Extensive and costly operating room sterilization procedures are thus significantly reduced, and patient comfort and treatment can be enhanced by controlling the temperature and humidity of the atmosphere provided beneath the film sheet. An "Arm and Hand Rest Device for Microsurgery" is detailed in U.S. Pat. No. 4,018,217, to Daniel R. Evans. The device includes an arm and hand rest for performing microsurgery such as an eye operation, on a patient lying on an operating table. The device has a board placed on the operating table beneath the upper body portion of the patient so that the weight of the patient will hold the device firmly in place. Two tables are disposed at the head end of the board and each includes a platform upon which the hands and arms are rested while the surgeon uses a scalpel or other instrument in performing the operation. The tables are spaced from one another to define the area in which the patient's head is placed for the operation and the platforms are adjustable vertically and have projections at the top end, extending toward each other. A "Vacuum Barrier" is detailed in U.S. Pat. No. 4,936,318, dated Jun. 26, 1990, to Arnold Schoolman. The device includes a protective apparatus for preventing the exchange of harmful substances between an area isolated by the apparatus and the environment, for use in medical laboratory and industrial applications. The apparatus includes a physical shield, a vacuum barrier and an adjustable support frame. It further includes a vacuum connector for connecting the apparatus to a vacuum source, a vacuum conduit for flow communicating with the air around the perimeter of the physical shield, such that the vacuum source draws air with the solid and liquid matter entrained in the air into the vacuum conduit, and multiple vacuum apertures located along the vacuum conduit for communicating the vacuum source with the air. The apparatus is designed to provide protection for persons in proximity to a source of harmful substances such as aerosols produced by surgical procedures at a surgical incision on a patient infected with the AIDS virus or the like. A "Surgical Instrument Tray" is detailed in U.S. Pat. No. 5,005,590, dated Apr. 9, 1991, to John D. Eldridge, et al. The device includes a retainer and method of producing a retainer, which retainer cooperates with either a magnetic or non-magnetic surgical drape to hold instruments during surgical operations. A rectangular tray includes a wall which extends from the periphery of the base portion. The polypropylene base portion is thermally bonded to a thermoplastic rubber retainer to sandwich magnetic elements therebetween. The magnetic elements are magnetically attached to a magnetic drape and thus, secure the retainer in any desired orientation with respect to the drape. The method includes vacuum-forming a thermoplastic shell over a tray-configured mold to sandwich a magnetic element between the thermoplastic shell and the retainer. My U.S. Pat. No. 5,322,072, dated Jun. 21, 1994, details a "Sterility Maintenance Cover, Surgical Instrument Tray and Drape Support". The device includes an L-shaped member having a base panel for fitting beneath the patient and upward-standing side or end panel and a horizontally-oriented instrument platform extending from the side or end panel above the patient's head, neck and shoulders for receiving instruments during surgery. The device facilitates draping the patient's head to insure a sterile operating field which is maintained throughout the surgical procedure. In a preferred embodiment the instrument panel and the end or side panels may be removed from the base panel. The December 1973 issue of Interiors Magazine at Page 52 details a one-piece plate glass panel bent into a simple U-shaped table such as a coffee table or the like.

It is an object of this invention to provide a new and improved device for maintaining surgical sterility during examination and surgical procedures in the head, shoulder and upper torso area of a patient.

Another object of the invention is to provide a new and improved sterility maintenance cover and instrument support which is preferably, but not necessarily constructed of a clear, radiolucent plastic material and includes a base panel for fitting on a flat surface such as an examination or operating table and selectively under the head, neck and shoulders, as well as the torso, thighs and feet of a patient, an upward-standing end panel extending from the base panel and fitted with an open window for accessing the patient from the side or end of the table and an instrument panel or platform extending from the end panel substantially parallel to the base panel, over the head and neck of the patient for receiving and containing instruments during the invasive or non-invasive procedure.

Yet another object of this invention is to provide a new and improved sterility maintenance cover and instrument support for effecting surgical sterility in draping of a patient during certain examination procedures and surgical operations and supporting medical instruments, which cover is characterized by a generally L-shaped, one-piece, preferably transparent and radiolucent plastic support device, the base panel of which selectively fits on an operating table under the head, neck and upper back or the torso, legs and feet of the patient and an end panel having an open access window and curving upwardly from the base panel, with an instrument panel or platform curving from the end panel over the patient's head and neck, for example, and further including gussets extending in spaced relationship with respect to each other between the base panel and instrument platform along the end panel, wherein the instrument platform supports and deploys the medical instruments and apparatus, as well as the drape or drapes, during the operation.

SUMMARY OF THE INVENTION

These and other objects of the invention are provided in a new and improved sterility maintenance cover and instrument support for draping a patient in a sterilized manner during surgery and supporting examination and/or surgical instruments. The instrument cover is characterized by a one-piece, transparent or opaque, radiolucent, polymeric device shaped to define a flat base panel for seating on the examination or operating table, normally beneath the head, neck and shoulders of a patient; an end panel projecting upwardly in fixed relationship from the base panel and having an open patient access window; and an instrument platform extending horizontally from the end panel substantially parallel to the base panel over the patient's head and neck for receiving one or more drapes, with a lip provided on the instrument platform to receive and contain examination, surgical and/or accessory instruments during examination and/or an operation performed on the patient. Transparent or opaque and radiolucent gussets may be provided between the base panel and the instrument platform along the parallel edges of the end panel to provide additional support for the instrument platform.

BRIEF DESCRIPTION OF THE DRAWING

The invention will be better understood by reference to the accompanying drawing, wherein.

DESCRIPTION OF THE PREFERRED EMBODIMENTS

Figure 1:
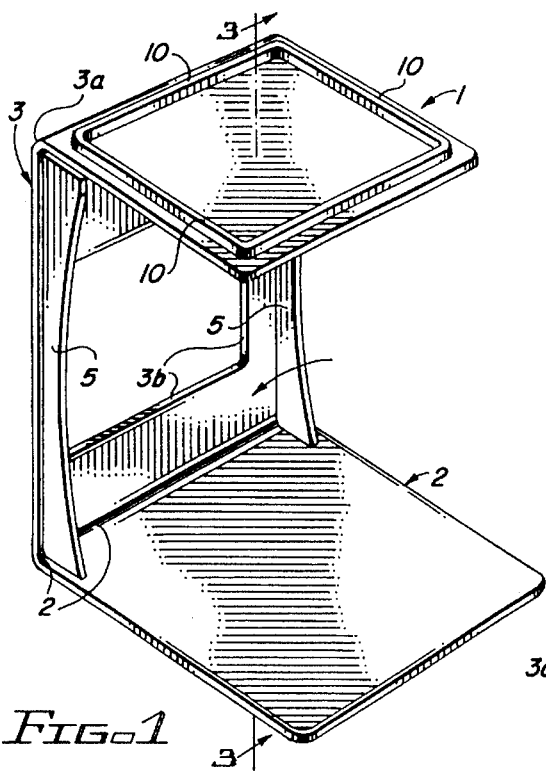
FIG. 1 is a perspective view of a preferred embodiment of the sterility maintenance cover and instrument support of this invention.
Figure 2:
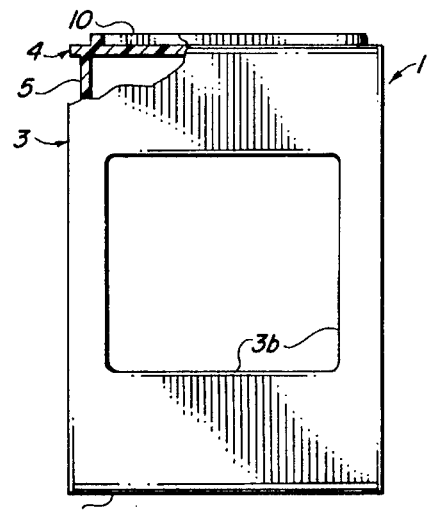
FIG. 2 is a rear view, partially in section, of the sterility maintenance cover and instrument support illustrated in FIG. 1.

Referring initially to FIGS. 1 and 2 of the drawing, in a preferred embodiment the sterility maintenance cover and instrument support of this invention is generally illustrated by reference numeral 1. The sterility maintenance cover and instrument support 1 is constructed of a preferably transparent, preferably radiolucent or opaque material such as polyethylene, polypropylene, "Plexiglass" (trademark), "Lexan" (trademark), ABS plastic (acrylonitrile-butadiene-styrene polymer) or other polymeric or alternative material which is well known to those skilled in the art. Wood, metal and fiberglass are alternative materials of construction, depending upon application of the device. The sterility maintenance cover and instrument support 1 includes a flat base panel 2 designed to lie flat on an examination or operating table 17 beneath the head, neck and shoulders of a patient 16, as illustrated. An end panel 3 curves upwardly from the base panel 2 at a base panel bend 2a and an instrument platform 4 extends from the top of the end panel 3 at an end panel bend 3a, substantially parallel to the base panel 2, over the head of the patient 16. One or more preferably transparent, preferably radiolucent gussets 5 may be extended between the base panel 2 and the instrument platform 4 at the base panel bend 2a and end panel bend 3a along the end panel 3, to better support the instrument platform 4 in substantially parallel relationship with respect to the base panel 2, for purposes which will be hereinafter further described. Furthermore, as illustrated in FIGS. 1 and 2, an open end panel window 3b is provided in the end panel 3 to facilitate convenient access to the patient 16 lying beneath the instrument platform 4. Moreover, a platform lip 10 is provided around the periphery of the instrument platform 4 to contain various instruments (not illustrated) during a desired examination and/or non-invasive or invasive procedure. Accordingly, it will be appreciated by those skilled in the art that the instrument platform 4 serves to support a drape 15, illustrated in phantom in FIG. 3, as well as an instrument tray (not illustrated) for positioning various types of instruments and accessory items (not illustrated) used in an examination and/or surgical procedure. This design facilitates close access of the instruments to the patient 16, as well as the attending nurses, anesthesiologist, doctor and surgeon. Furthermore, in a preferred embodiment the transparency of the instrument platform 4 and the end panel 3, as well as the open end panel window 3b, allow observation of, and access to the patient at all times by the anesthesiologist, as well as the surgeon and attending physicians and nurses.

Figure 3:
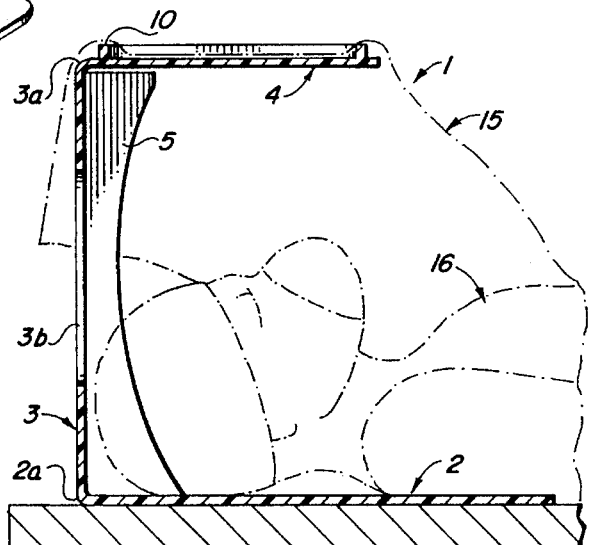
FIG. 3 is a sectional view taken along line 3—3 of the sterility maintenance cover and instrument support illustrated in FIG. 1 and placed on an examination or operating table.
Figure 4:
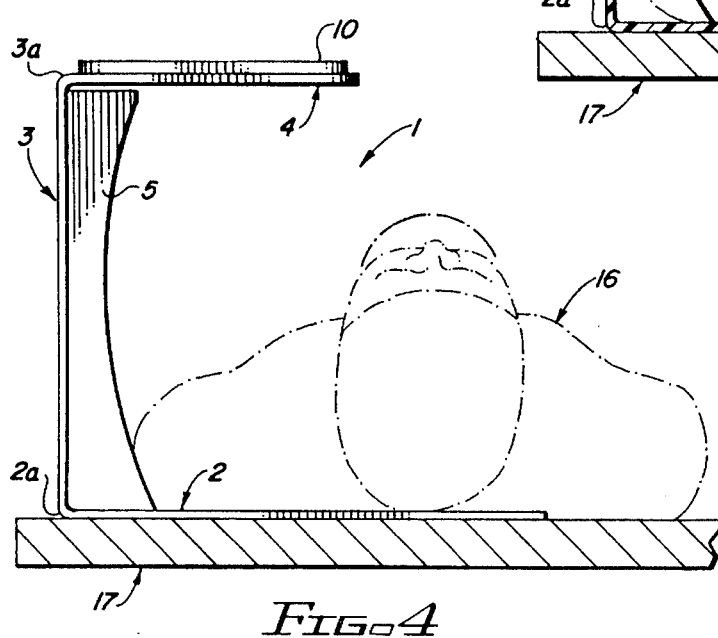
FIG. 4 is a right side view of the sterility maintenance cover and instrument support illustrated in FIG. 1 and placed on an examination or operating table.
Figure 5:
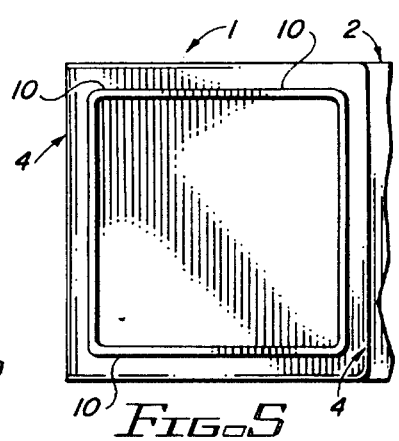
FIG. 5 is a top view, partially in section, of the sterility maintenance cover and instrument support illustrated in FIG. 1.

Referring again to FIG. 1 and also to FIGS. 3 and 4 of the drawing, the optional gussets 5 may be shaped for extension between the instrument platform 4 and the base panel 2 along the parallel edges of the end panel 3 to support the instrument platform 4 in the desired substantially horizontal position with respect to the base panel 2. The gussets 5 may typically be shaped of the same material, preferably the transparent and radiolucent plastic material used to construct the base panel 2, end panel 3 and instrument platform 4 and may be glued or otherwise attached to the base panel 2, end panel 3 and instrument platform 4, according to the knowledge of those skilled in the art.

It will be further appreciated by those skilled in the art that the sterility maintenance cover and instrument support of this invention facilitates quick and easy support of instruments and/or draping of either the head, torso or legs and feet of a patient for various types of examination procedures and/or operations, including routine examinations, emergency room procedures, intensive care and home care conditions and surgical procedures such as pacemaker implants, heart catherization procedures, open heart surgery and other surgical procedures, in non-exclusive particular. Because the end panel 3 and the instrument platform 4 elements of the sterility maintenance cover and instrument support 1 are preferably transparent, and due to the open end panel window 3b, the patient may be viewed and accessed at all times during the operation by the anesthesiologist, cardiologist or surgeon and the other attending physicians and nurses, as deemed necessary. Moreover, the sterility maintenance cover and instrument support 1 can be constructed of a single panel of desired material, preferably transparent and radiolucent plastic material and alternatively positioned as illustrated in FIGS. 3 and 4, depending upon the particular type of access desired to the patient 16. In a most preferred embodiment, a single sheet of transparent, radiolucent polymeric material such as "Plexiglass", "Lexan" or other transparent plastic, in non-exclusive particular, of sufficient thickness to lend sufficient structural integrity to the device, can be utilized, such that the sterility maintenance cover and instrument support 1 may be manufactured from a single piece of material wherein the base panel 2, end panel 3, and the instrument panel 4 are shaped at the base panel bend 2a and end panel bend 3a, according to techniques which are well known to those skilled in the art. A typical, but not exclusive, size for the sterility maintenance cover and instrument support 1 is 15 inches from the top of the instrument platform 2 to the bottom of the base panel 2 and 12 inches in width, with an end panel window 3b about 7 inches square and a base panel 2 length of 12 inches. The thickness of the sheet of plastic or alternative material from which the base panel 2, end panel 3 and instrument platform 4 are shaped, typically ranges from about one-fourth of an inch to about one-half of an inch, depending upon the structural integrity of the transparent plastic material chosen.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A device for supporting instruments over a supine patient on a surface, comprising a base panel for insertion beneath the patient and the surface; a support panel extending upwardly from one end of said base panel; an opening provided in said support panel for accessing the patient; and an instrument platform extending from one end of said support panel over at a portion of the patient, said instrument platform having two sides and a free end, for supporting the instruments above the patient.

2. The device of claim 1 comprising lip means projecting from said instrument platform for containing the instruments on said instrument platform.

3. The device of claim 2 wherein said lip means projects from said sides and said free end of said instrument platform for containing the instruments on said instrument platform.

4. The device of claim 3 comprising support means engaging said base panel and said instrument platform for spacing said instrument platform from said base panel.

5. The device of claim 4 wherein at least said support panel and said instrument platform are transparent and said support means comprises a pair of gussets attached in spaced relationship with respect to each other to said base panel, said support panel and said instrument platform.

6. The device of claim 1 comprising support means engaging said base panel and said instrument platform for spacing said instrument platform from said base panel.

7. The device of claim 6 comprising lip means projecting from said instrument platform for containing the instruments on said instrument platform.

8. The device of claim 6 wherein said support means comprises a pair of gussets attached in spaced relationship with respect to each other to said base panel, said support panel and said instrument platform.

9. The device of claim 8 comprising lip means projecting from said instrument platform for containing the instruments on said instrument platform.

10. The device of claim 1 wherein said base panel, said support panel and said instrument platform are shaped from a one-piece, transparent and radiolucent plastic material.

11. The device of claim 10 comprising lip means projecting from said instrument platform for containing the instruments on said instrument platform.

12. The device of claim 11 comprising support means engaging said base panel and said instrument platform for spacing said instrument platform from said base panel.

13. The device of claim 12 wherein said support means comprises a pair of gussets attached in spaced relationship with respect to each other to said base panel, said support panel and said instrument platform.

14. A device for supporting a drape and maintaining sterility of a patient lying on a table, comprising a base panel for insertion between the head, neck and shoulders of the patient and the table; a support panel curving upwardly from said base panel; an open window provided in said support panel for accessing the patent; and an instrument platform curving from said support panel over at least the head of the patient and extending substantially parallel to said base panel, said instrument platform having two sides and a free end for supporting the drape.

15. The device of claim 14 comprising a lip upwardturned from the periphery of said instrument platform for containing medical instruments and wherein at least said support panel and said instrument platform are radiolucent.

16. The device of claim 15 wherein at least said support panel and said instrument platform are transparent and comprising support means engaging said base panel and said instrument platform for spacing said instrument platform from said base panel.

17. The device of claim 16 wherein said support means comprises a pair of transparent and radiolucent gussets attached in spaced relationship with respect to each other to said base panel, said support panel and said instrument platform.

18. The device of claim 14 wherein said support means comprises a pair of transparent and radiolucent gussets attached in spaced relationship with respect to each other to said base panel, said support panel and said instrument platform.

19. A device for supporting a drape, maintaining sterility of a patient lying on an examination or operating table and supporting medical instruments over the patient, said device comprising a one-piece, transparent and radiolucent panel characterized by a base panel for insertion between the head, neck and shoulders of the patient and the table; a support panel extending upwardly from said base panel; an open window provided in said support panel for accessing the patent; and an instrument platform extending from said support panel over at least the head of the patient, said instrument platform having two sides and a free end for supporting the drape and the medical instruments; and a lip upward turned from said two sides and said free end of said instrument platform, for containing the medical instruments on the instrument platform.

20. The device of claim 19 comprising support means engaging said base panel and said instrument platform for spacing said instrument platform from said base panel.

* * * * *